United States Patent [19]

Peseckis et al.

[11] Patent Number: 5,002,949
[45] Date of Patent: Mar. 26, 1991

[54] 5-SUBSTITUTED-6-AMINOPYRIMIDINE DERIVATIVES

[75] Inventors: Steven M. Peseckis, Plainsboro; Jehan F. Bagli, Princeton, both of N.J.; Richard J. Heaslip, Newtown; Thomas J. Colatsky, Devon, both of Pa.

[73] Assignee: American Home Products Corporation, New York, N.Y.

[21] Appl. No.: 517,099

[22] Filed: May 1, 1990

[51] Int. Cl.$^5$ ................. A61K 31/505; C07D 239/02
[52] U.S. Cl. ................. 514/256; 514/269; 544/319; 544/328
[58] Field of Search ................. 544/319, 328; 514/272, 514/256, 269

[56] References Cited

U.S. PATENT DOCUMENTS

| | | | |
|---|---|---|---|
| 3,968,214 | 7/1976 | Claverie et al. | 544/320 X |
| 4,073,905 | 2/1978 | Kummer et al. | 544/320 X |
| 4,505,910 | 3/1985 | Bagli | 514/26 |
| 4,617,393 | 10/1986 | Bagli et al. | 544/319 |

OTHER PUBLICATIONS

Derwent 14713S-B Abstract of JA-7106576-R.
Uchiyama et al., Stroke, 14 (4), 511 (1983).

Primary Examiner—Frederick E. Waddell
Assistant Examiner—Catherine S. Kilby Scalzo
Attorney, Agent, or Firm—Richard K. Jackson

[57] ABSTRACT

A compound of the formula:

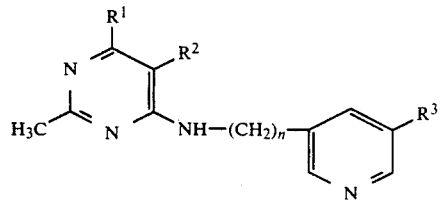

in which
$R^1$ is —OH or —NH$_2$; $R^2$ is a halogen or —CN; $R^3$ is a halogen or —CN; and n is one of the integers 1, 2 or 3; or a pharmaceutically acceptable salt thereof, are useful as antithrombotic agents.

10 Claims, No Drawings

5-SUBSTITUTED-6-AMINOPYRIMIDINE DERIVATIVES

BACKGROUND OF THE INVENTION

Extensive evidence exists today to implicate blood platelet aggregation in the development of thrombosis and transient ischemia. Uchiyama et al., Strokes 14, 511 (1983). Compounds which are capable of preventing and/or disrupting and dispersing platelet aggregations are useful antithrombotic agents for treatment of stroke, cerebral thrombosis, unstable angina and peripheral vascular diseases.

DESCRIPTION OF THE INVENTION

In accordance with this invention, there is provided a group of novel anti-thrombotic agents of the formula:

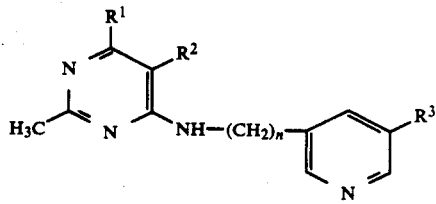

in which
$R^1$ is —OH or —$NH_2$;
$R^2$ is a halogen or —CN;
$R^3$ is a halogen or —CN;
and
n is one of the integers 1,2 or 3; or a pharmaceutically acceptable salt thereof.

The halogen substituents of these compounds may be chlorine, fluorine, bromine or iodine, chlorine or bromine being preferred. The pharmaceutically acceptable salts are derived from those organic or inorganic acids such as hydrochloric, hydrobromic, sulfuric, phosphoric, nitric, methanesulfonic, ethanesulfonic, hydroxyethanesulfonic, toluene sulfonic, naphthalenesulfonic, formic, acetic, propionic, oxalic, succinic, glycollic, lactic, malic, tartaric, citric, ascorbic, maleic, hydroxymaleic, pyruvic, phenylacetic, benzoic, para-amino benzoic, parahydroxybenzoic, salicylic, sulfanilic acids, and the like known to provide acceptable salts. In addition, those compounds capable of enolization can form pharmaceutically acceptable salts with acceptable basis such as alkali metal hydroxides (NaOH, KOH, etc.) or alkaline earth metal hydroxides (Ca(OH)$_2$, Mg(OH)$_2$, etc.), ammonia or mono- or dialkylamines in which the alkyl groups contain from 1 to 6 carbon atoms.

In addition to the novel compounds of this invention, there is provided a method for using these compounds, as well as the corresponding compounds where $R^3$ is hydrogen and especially where $R^2$ is —CN and $R^3$ is hydrogen which compounds are disclosed in U.S. Pat. No. 4,505,910, by administering them to a mammal in need thereof, orally or parenterally, in an amount sufficient to inhibit blood platelet aggregation and thrombus formation.

The compounds of this invention are prepared by conventional methods routinely employed by the medicinal chemist. In general, the most convenient method for preparing the desired compounds involves the displacement of a good leaving group (L) in 6-position of the pyrimidinone ring, thusly:

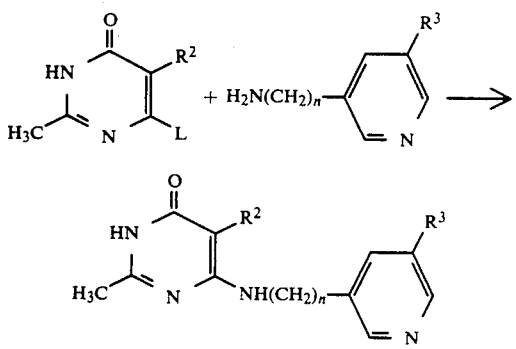

where L is —Cl, —$SCH_3$, and the like. This reaction is generally performed at elevated temperatures (50° C. to reflux) for extended periods of time (10 to 30 hours). The reactants are either known compounds or are prepared routinely by literature methods, unless their detailed preparation is provided in the following specific examples which are provided by way of illustration rather than limitation.

EXAMPLE 1

5-Bromo-6-[[(5-bromo-3-pyridinyl)methyl]amino]-2-methyl-4(3H)-pyrimidone

A stirred mixture of 5-bromo-6-chloro-2-methyl-4-pyrimidinol (4.54 g, 20.3 mmol) and 5-aminomethyl-3-bromopyridine (11.4 g, 61.0 mmol) in 1,2-dimethoxyethane (40 mL) was heated at reflux for 18 hours. The mixture was cooled to 23° C. The precipitate which formed was isolated, rinsed with 1,2-dimethoxyethane and water, and then recrystallized from methanol to provide the title compound as a white, analytically pure product (5.16 g, 13.8 mmol, 68% of theory): mp 241–242 C.; $R_f$ 0.62 (20% MeOH in EtOAc); $^1$H NMR (DMSO-D$_6$, 400 MHz)$\delta$8.56 (d, J=2 Hz, 1H), 8.49 (d, J=2 Hz, 1H), 7.92 (m, 1H), 7.33 (t, J=6 Hz, 1H), 4.55 (d, J=6 Hz, 2H), 2.16 (s, 3H); IR (KBr) 3400 (NH), 2700–3000 (CH), 1640 (C=O) cm$^{-1}$; UV (MeOH)$\lambda$278 ($\epsilon$12,400); mass spectrum m/e 372 (M+, 54%), 374 (M+, 100%), 376 (M+, 52%), 185 (C$_6$H$_6$BrN$_2$, 78%).

Elemental analysis for: C$_{11}$H$_{10}$Br$_2$N$_4$O: Calc'd: C, 35.32; H, 2.69; N, 14.98. Found: C, 35.23; H, 2.79; N, 14.94.

EXAMPLE 2

5-[[(5-Bromo-3,6-dihydro-2-methyl-6-oxo-4-pyrimidinyl)amino]methyl]-3-pyridinecarbonitrile A stirred mixture of 5-hydroxymethyl-3-bromopyridine (8.50 g, 45.2 mmol) and copper (I) cyanide (10.1 g, 11.3 mmol) in pyridine (50 mL) was heated in a sealed pressure reaction vessel at 165° C. for 20 hours. After cooling to 23° C., the mixture was diluted with concentrated ammonium hydroxide (15 mL) and saturated aqueous ammonium chloride (60 mL), after stirring for 2 hours, the mixture was treated with chloroform (50 mL) and allowed to set for 72 hours. The aqueous layer was then extracted with chloroform. The combined organic extracts were dried (MgSO$_4$), filtered, and concentrated in vacuo. The residue was purified by flash chromatography (silica gel, 2 inch column, 4:1 EtOAc:hexane as eluant) followed by crystallization from diethyl ether to afford 5-hydroxymethyl-3-pyridinecarbonitrile (5.42 g, 40.4 mmol, 89% yield): $R_f$ 0.49

(EtOAc); $^1$H NMR (CDCl$_3$, 200 MHz)$\delta$8.80 (m, 2H), 8.03 (s, 1H), 4.83 (s, 2H).

A solution of 5-hydroxymethyl-3-pyridinecarbonitrile (4.39 g, 32.7 mmol) in diethyl ether (250 mL) at 23° C. was saturated with gaseous HCl. Solvent was then removed in vacuo and the residue was suspended in thionyl chloride (14.3 mL, 196 mmol). The mixture was then heated at reflux for 2 hours, cooled to 23° C., and diluted with benzene (150 mL). The tan precipitate was isolated by filtration, transferred to a pressure reactor, and dissolved in methanol (30 mL). The methanolic solution was saturated with gaseous ammonia, sealed in the reaction vessel, and heated with stirring at 80° C. for 2.5 hours. After cooling to 23° C., the solution was again saturated with gaseous ammonia, sealed in the vessel, and heated at 80° C. for 5 hours. The reaction mixture was then concentrated in vacuo, and the residue was diluted with aqueous 0.5M NaOH (60 mL). The aqueous layer was extracted with chloroform (3×60 mL). The combined organic extracts were dried (MgSO$_4$), filtered, and concentrated in vacuo to provide 5-aminomethyl-3-pyridinecarbonitrile (2.79 g, 21.0 mmol, 64% yield): R$_f$0.19 (20% MeOH in EtOAc); $^1$H NMR (DMSO-D$_6$, 200 MHz)$\delta$8.88 (dd, J=7,2 Hz, 1H), 8.79 (m, 1H), 8.25 (d, J=7 Hz), 3.75 (s, 2H), 2.8 (br s, 2H).

A stirred suspension of 5-bromo-6-chloro-2-methyl-4-pyrimidinol (1.57 g, 7.04 mmol), 5-cyano-3-aminomethylpyridine (1.03 g, 7.74 mmol), and 2,6-lutidine (2.00 mL, 17.4 mmol) in 1,2-dimethoxyethane (7.0 mL) was heated at 90° C. for 15 hours. Solvent was removed in vacuo, and the residue was suspended in water. The white precipitate was isolated by filtration with aqueous rinse, and then recrystallized from methanol/diethyl ether to afford crude product (922 mg, 41%). The crude product was adsorbed onto silica gel. The product was eluted with 4:1 ethyl acetate:hexane (150 mL) followed by methanol (300 mL). The methanol eluant was concentrated in vacuo, and the residue was recrystallized from methanol/diethyl ether to give the title compound in analytically pure form (705 mg, 2.20 mmol, 31% yield): mp 260.0°-260.5° C.; R$_f$ 0.51 (20% MeOH in EtOAc); $^1$H NMR (DMSO-D$_6$, 400 MHz)$\delta$11.0 (s, 1H), 8.88 (d, J=1.69 Hz, 1H), 8.77 (d, J=1.64 Hz, 1H), 8.16 (s, 1H), 7.34 (t, J=6.14 Hz, 1H), 4.60 (d, J=6.00 Hz, 2H), 2.16 (s, 3H); IR (KBr) 3280 (NH), 2620-3000 (CH), 2230 (CN), 1645, 1605, 1585 (C=C, C=N); UV (MeOH)$\lambda$275.5 ($\epsilon$10900).

Elemental analysis for: C$_{12}$BrN$_5$O: Calc'd: C, 45.02; H, 3.15; H, 21.88. Found: C, 45.25; H, 3.44; N, 21.50.

EXAMPLE 3

6-[[(5-bromo-3-pyridinyl)methyl]amino]-1,4-dihydro-2-methyl-4-oxo-5-pyrimidinecarbonitrile A stirred suspension of 6-thiomethyl-1,4-dihydro-2-methyl-4-oxo-5-pyrimidinecarbonitrile (1.08 g, 5.96 mmol) and 5-aminomethyl-3-bromopyridine (2.79 g, 14.9 mmol) in 1,2-dimethoxyethane (15 mL) was heated at reflux for 72 hours. The mixture, at 23° C., was diluted with water. The solids were isolated by filtration with aqueous rinse, heated to 40° C. in MeOH/CHCl$_3$, reisolated by filtration with CHCl$_3$ rinse, and dried in vacuo to provide the title compound as a pure product (730 mg, 2.28 mmol, 38% yield): mp>300° C.; $^1$H NMR (DMSO-D$_6$, 400 MHz)$\delta$12.3 (br s, 1H), 8.58 (d, J=2.1 Hz, 1H), 8.50 (d, J=1.5 Hz, 1H), 8.38 (t, J=5.7 Hz, 1H, NH), 7.96 (t, J=1.7 Hz, 1H), 4.59 (d, J=5.9 Hz, 2H), 3.32 (s, 3H); IR (KBr) 3320 (NH), 2700-3020 (CH), 2225 (CN), 1675, 1595 (C=C, C=N); mass spectrum m/e 321 (M$^+$, 36%), 319 (M$^+$, 35%).

Elemental analysis for C$_{12}$H$_{10}$BrN$_5$O: Calc'd: C, 45.02; H, 3.15; N, 21.88. Found: C, 45.21; H, 3.16; N, 21.64.

EXAMPLE 4

6-[[(5-Bromo-3-pyridinyl)methyl]amino]-5-chloro-2-methyl-4(1H)-pyrimidone

A stirred mixture of 5,6-dichloro-2-methyl-4-pyrimidinol (1.20 g, 6.70 mmol) and 5-aminomethyl-3-bromopyridine (3.65 g, 19.5 mmol) in dimethoxyethane (25 mL) was heated at reflux for 14 hours. The mixture was then concentrated in vacuo and diluted with water. The precipitate was isolated by filtration with aqueous rinse, recrystallized twice from ethyl acetate, and then recrystallized a third time, but from methanol, to provide the title compound as a pure product (1.07 g, 3.25 mmol, 48%): mp 274°-275° C.; R$_f$0.59 (20% MeOH in EtOAc); $^1$H NMR (DMSO-D$_6$, 400 MHz)$\delta$11.9 (br s, 1H), 8.57 (d, J=2 Hz, 1H), 8.49 (s, 1H), 7.93 (s, 1H), 7.46 (t, J=6 Hz, 1H), 4.56 (d, J=6.1 Hz, 2H), 2.18 (s, 3H); IR (KBr) 3300 (NH), 2790-3000 (CH), 1660, 1615, 2590 (C=C, C=N); mass spectrum m/e 329.8 (M$^+$, 70%), 292.9 (M$^+$−Cl, 32%).

Elemental analysis for: C$_{11}$H$_{10}$BrClN$_4$O: Calc'd: C, 40.09; H, 3.06; N, 17.00. Found: C, 39.88; H, 3.32; N, 16.96.

EXAMPLE 5

5-Bromo-N-[[(5-bromo-3-pyridinyl)methyl]amino]-2-methyl-4,6-pyrimidinediamine

A stirred suspension of 4,6-dichloro-2-methylpyrimidine (39.5 g, 244 mmol) in 1,2-dimethoxyethane (50 mL) in a sealable pressure reaction vessel was treated with concentrated aqueous ammonium hydroxide (40 mL). The mixture was vigorously stirred at 23° C. for 14 days in the sealed vessel. The mixture was then diluted with water and filtered. The isolated white solids were rinsed with water and dried in vacuo to afford 6-chloro-2-methyl-4-aminopyrimidine (20.94 g, 146 mmol, 60% yield): mp 191°-192° C.; R$_f$ 0.49 (EtOAc); $^1$H NMR (DMSO-D$_6$, 200 MHz)$\delta$7.09 (br s, 2H, NH), 6.24 (s, 1H), 2.26 (s, 3H).

A stirred mixture of 6-chloro-2-methyl-4-aminopyrimidine (1.15 g, 8.03 mmol) and 5-aminomethyl-3-bromopyridine (4.51 g, 24.1 mmol) was heated at 120° C. for 16 hours. The mixture was purified by flash chromatography (silica gel, EtOAc, then 10% MeOH in EtOAc as eluants) to give N-[[(5-bromo-3-pyridinyl)methyl]amino]-2-methyl-4,6-pyrimidinediamine (2.03 g, 6.90 mmol, 86%): R$_f$0.38 (20% MeOH in EtOAc); $^1$H NMR (DMSO-D$_6$, 200 MHz)$\delta$8.55 (s, 1H), 8.50 (s, 1H), 7.93 (s, 1H), 7.08 (t, J=6 Hz, 1H), 6.02 (s, 2H), 5.20 (s, 1H), 4.40 (d, J=6 Hz, 2H), 2.15 (s, 3H).

To a mixture of N-[[(5-bromo-3-pyridinyl)methyl]amino]-2-methyl-4,6-pyrimidinediamine (1.00 g, 3.40 mmol) in carbon tetrachloride (50 mL) at 23° C. was added N-bromosuccinimide (0.61 g, 3.90 mmol). The mixture was stirred for 1.5 hours at 23° C. and then filtered. The isolated solid was purified by flash chromatography (silica gel, 1:1 EtOAc:CHCl$_3$ then 20% MeOH in EtOAc as eluants) and two recrystallizations from methanol to provide the title compound (376 mg, 1.01 mmol, 30%): mp 221°-222° C., R$_f$ 0.69 (20% MeOH in EtOAc); $^1$H NMR (DMSO-D$_6$, 400

MHz)δ8.54 (d, J=2 Hz, 1H), 8.50 (d, J=2 Hz, 1H), 7.93 (m, 1H), 7.09 (t, J=6 Hz, 1H), 6.39 (s, 2H), 4.51 (d, J=6 Hz, 2H), 2.13 (s, 3H); IR (KBr) 3480, 3300 (NH), 2900-3150 (CH), 1650, 1600 (C=C, C=N) cm$^{-1}$; mass spectrum m/e 375 (M+, 45%), 373 (M+, 84%), 371 (M+, 44%), 292 ($C_{11}H_{11}BrN_5$, 54%), 185 ($C_6H_6BrN_2$, 50%).

Elemental analysis for: $C_{11}H_{11}Br_2N_5$: Calc'd: C, 35.42; H, 2.97; N, 18.77. Found: C, 35.42; H, 2.96; N, 18.96.

EXAMPLE 6

4-Amino-6-[[(5-Bromo-3-pyridinyl)methyl]amino]-2-methyl-5-pyrimidinecarbonitrile A suspension of 6-thiomethyl-1,4-dihydro-2-methyl-4-chloro-5-pyrimidinecarbonitrile (15.0 g, 75.2 mmol) in 1,2-dimethoxyethane (40 mL) was treated with concentrated ammonium hydroxide (40 mL) and sealed in a pressure reaction vessel. The mixture was heated at 75° C. (pressure~50 psi) for 5 hours, cooled to 23° C., and let stand at 23° C. for 16 hours. The solids were isolated by filtration with aqueous rinse and recrystallized from methanol to afford 4-amino-6-thiomethyl-2-methyl-5-pyrimidinecarbonitrile (8.66 g, 48.8 mmol, 64% yield). An additional recrystallization from methanol provided analytically pure material. $^1$H NMR (DMSO-D$_6$, 400 MHz)δ7.67 (br s, 2H), 2.51 (s, 3H), 2.36 (s, 3H); IR (KBr) 3380, 3355 (NH), 3110, 2920, 2850, 2760 (CH), 2210 (CN), 1675 (C=C, C=N) cm$^{-1}$; UV (MeOH) λ279.0 (ε6650); mass spectrum m/e 180 (M+, 100%).

Elemental analysis for: $C_7H_8N_4S$: Calc'd: C, 46.65; H, 4.47; N, 31.09. Found: C, 46.67; H, 4.80; N, 31.42.

A stirred mixture of 4-amino-6-thiomethyl-2-methyl-5-pyrimidinecarbonitrile (1.60 g, 8.91 mmol) and 5-aminomethyl-3-bromopyridine (5.00 g, 26.7 mmol) was heated at 165° C. for 18 hours. The mixture was diluted with water, heated briefly to approximately 80° C., and then cooled to 23° C. The solids were isolated, rinsed with methanol and chloroform, and recrystallized from methanol to afford the title compound (1.55 g, 4.86 mmol, 53% yield): mp 283°-284° C.; R$_f$0.54 (EtOAc); $^1$H NMR (DMSO-D$_6$, 400 MHZ)δ8.56 (d, J=2 Hz, 1H), 8.50 (d, J=2 Hz, 1H), 7.95 (m, 1H), 7.85 (t, J=6 Hz, 1H), 7.17 (s, 2H), 4.54 (d, J=6 Hz, 2H), 2.17 (s, 3H); IR (KBr) 2900-3100 (CH), 2200 (CN), 1660, 1600 (C=C, C=N) cm$^{-1}$; mass spectrum m/e 318 (M+, 100%), 320 (M+, 99%), 185 ($C_6H_6BrN_2$, 62%).

Elemental analysis for: $C_{12}H_{11}BrN_6$: Calc'd: C, 45.16; H, 3.47; N, 26.33. Found: C, 45.38; H, 3.17; N, 26.43.

The antithrombotic activity of the compounds of this invention was established by demonstrating their ability to inhibit platelet aggregation induced by epinephrine, adenosine diphosphate, arachidonic acid, U46619 (endoperoxide) and collagen, in accordance with standard test procedures. As representative compounds, 5-bromo-6-[[(5-bromo-3-pyridinylmethyl]amino]-2-methyl-4(1H)-pyrimidinone, HBr (Compound A) and 5-cyano-2-methyl-6-[[(3-pyridinyl)methyl)]amino]-4(1H)-pyrimidinone hydrochloride (Compound B) inhibited platelet aggregation as follows.

TABLE A

| | IC$_{50}$ μM | |
|---|---|---|
| | Compound A | Compound B |
| Epinephrine (second phase) | 0.43 | 10.8 |
| ADP (second phase) | 0.20 | 6.3 |
| Arachidonic Acid | 0.18 | 2.8 |
| U46619 (endoperoxide) | 0.21 | 6.6 |
| Collagen | 0.54 | 13.3 |

The effect of these compounds on the inhibition of white thrombus formation in the rabbit arteriovenous model demonstrated their effectiveness at reducing thrombus weight in vivo as follows:

TABLE B

| mg/kg i.v. | Compound A Percent Inhibition | Compound B Percent Inhibition |
|---|---|---|
| 0.1 | 28.4% | |
| 0.25 | 47.1% | |
| 0.5 | 59.7% | 41.7% |
| 1.0 | | 56.8% |
| 5.0 | | 76.7% |

Neither of these compounds demonstrate any physiologically meaningful effect on prothrombin time, activated partial thromboplastin time or thrombin clotting when tested with normal human plasma at 200 μg/ml.

Thus, the compounds of this invention are very potent inhibitors of blood platelet aggregation and are useful in preventing the formation of or maintenance of undesired thrombotic conditions in the mammal. As such, the compounds of this invention are useful on the treatment of and prevention of cerebral thrombosis, unstable angina and transient, peripheral ischemia when administered orally or parenterally to the mammal in need of such treatment.

The dosage to be employed may be administered neat or with a pharmaceutical carrier to a patient in need thereof. The pharmaceutical carrier may be solid or liquid.

A solid carrier can include one or more substances which may also act as flavoring agents, lubricants solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific vascular problem must be subjectively determined by the attending physician. The variables involved include the specific state of thrombosis formation or potential formation, the route of administration, and response pattern of the patient. Based upon the activity profile and potency of the compounds of this invention, an initial human i.v. dose within the range of about 0.01 to about 10 mg/kg/day, should be appropriate. The continuing dose may then be modified to achieve the desired effect, within the range of about 0.01 to about 5 mg/kg/day, as personalized for the patient.

What is claimed is:

1. A compound of the formula:

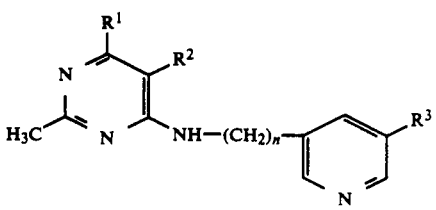

in which
$R^1$ is —OH or —NH$_2$;
$R^2$ is a halogen or —CN;
$R^3$ is a halogen or —CN;
and
n is one of the integers 1, 2 or 3; or a pharmaceutically acceptable salt thereof.

2. A compound of claim 1 of the formula:

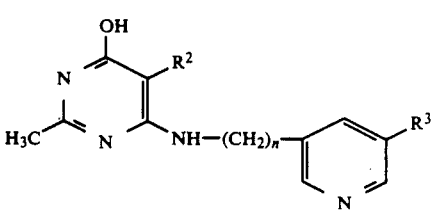

in which
$R^2$ is a halogen or —CN;
$R^3$ is a halogen or —CN;
and
n is one of the integers 1, 2 or 3; or a pharmaceutically acceptable salt thereof.

3. A compound of claim 1 of the formula:

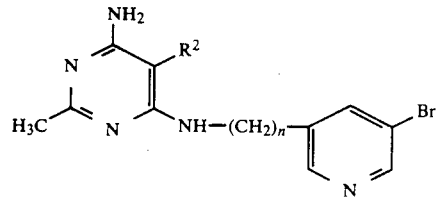

in which
$R^2$ is a halogen or —CN;
and
n is one of the integers 1, 2 or 3; or a pharmaceutically acceptable salt thereof.

4. The compound of claim 1 which is 5-bromo-6-[[(5-bromo-3-pyridinyl)methyl]amino]-2-methyl-4(3H)-pyrimidone, or a pharmaceutically acceptable salt thereof.

5. The compound of claim 1 which is 5-[[(5-bromo-3,6-dihydro-2-methyl-6-oxo-4-pyrimidinyl)amino]methyl]-3-pyridinecarbonitrile, or a pharmaceutically acceptable salt thereof.

6. The compound of claim 1 which is 6-[[(5-bromo-3-pyridinyl)methyl]amino]-1,4-dihydro-2-methyl-4-oxo-5-pyrimidinecarbonitrile, or a pharmaceutically acceptable salt thereof.

7. The compound of claim 1 which is 6-[[(5-bromo-3-pyridinyl)methyl]amino]-5-chloro-2-methyl-4(1H)-pyrimidone, or a pharmaceutically acceptable salt thereof.

8. The compound of claim 1 which is 5-bromo-N-[[(5-bromo-3-pyridinyl)methyl]amino]-2-methyl-4,6-pyrimidinediamine, or a pharmaceutically acceptable salt thereof.

9. The compound of claim 1 which is 4-amino-6-[[(5-bromo-3-pyridinyl)methyl]amino]-2-methyl-5-pyrimidinecarbonitrile, or a pharmaceutically acceptable salt thereof.

10. A method for inhibiting blood platelet aggregation and thrombus formation which comprises administering to a mammal in need thereof, orally or parenterally, an antithrombotic amount of a compound of the formula:

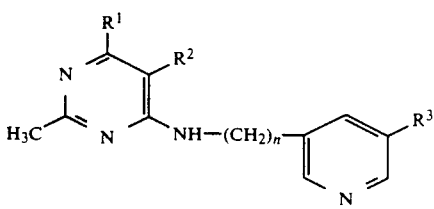

in which
$R^1$ is —OH or —NH$_2$;
$R^2$ is a halogen or —CN;
$R^3$ is hydrogen, halogen or —CN;
and
n is one of the integers 1, 2 or 3; or a pharmaceutically acceptable salt thereof.

* * * * *